US008527280B2

(12) United States Patent
Boesen

(10) Patent No.: US 8,527,280 B2
(45) Date of Patent: *Sep. 3, 2013

(54) VOICE COMMUNICATION DEVICE WITH FOREIGN LANGUAGE TRANSLATION

(76) Inventor: Peter V. Boesen, Des Moines, IA (US)

(*) Notice: Subject to any disclaimer, the term of this patent is extended or adjusted under 35 U.S.C. 154(b) by 1984 days.

This patent is subject to a terminal disclaimer.

(21) Appl. No.: 10/022,022

(22) Filed: Dec. 13, 2001

(65) Prior Publication Data

US 2003/0115068 A1 Jun. 19, 2003

(51) Int. Cl.
*G06F 17/20* (2006.01)
*H04R 25/00* (2006.01)

(52) U.S. Cl.
USPC ............. 704/277; 704/8; 381/313; 381/375

(58) Field of Classification Search
USPC ........... 704/270, 275, 277, 5, 8; 381/313, 381/370, 375, 387
See application file for complete search history.

(56) References Cited

U.S. PATENT DOCUMENTS

| | | | |
|---|---|---|---|
| 4,334,315 A | 6/1982 | Ono et al. | |
| 4,865,044 A | 9/1989 | Wallace et al. | |
| 5,295,193 A | 3/1994 | Ono | |
| 5,298,692 A | 3/1994 | Ikeda et al. | |
| 5,497,339 A | 3/1996 | Bernard | |
| 5,721,783 A * | 2/1998 | Anderson | 381/328 |
| 5,749,072 A | 5/1998 | Mazurkiewicz et al. | |
| 5,771,438 A | 6/1998 | Palermo et al. | |
| 5,929,774 A | 7/1999 | Charlton | |
| 5,933,506 A * | 8/1999 | Aoki et al. | 381/151 |
| 5,987,146 A | 11/1999 | Pluvinage et al. | |
| 6,021,207 A | 2/2000 | Puthuff et al. | |
| 6,081,724 A | 6/2000 | Wilson | |
| 6,094,492 A | 7/2000 | Boesen | |
| 6,112,103 A | 8/2000 | Puthuff | |
| 6,157,727 A * | 12/2000 | Rueda | 381/312 |
| 6,167,039 A | 12/2000 | Karlsson et al. | |
| 6,181,801 B1 | 1/2001 | Puthuff et al. | |
| 6,275,789 B1 | 8/2001 | Moser et al. | |
| 6,408,081 B1 | 6/2002 | Boesen | |
| D464,039 S | 10/2002 | Boesen | |
| 6,470,893 B1 | 10/2002 | Boesen | |
| D468,299 S | 1/2003 | Boesen | |

(Continued)

FOREIGN PATENT DOCUMENTS

EP 1017252 A2 * 7/2000

OTHER PUBLICATIONS

Rick Johnson, 5th International Conference on Wearable computing, Computing magazine, Aug. 2000.

(Continued)

*Primary Examiner* — Angela A Armstrong
(74) *Attorney, Agent, or Firm* — McKee, Voorhees & Sease, P.L.C.

(57) ABSTRACT

Methods and devices for voice communications and foreign language translation are disclosed. One method includes selecting one of a plurality of microphones of an earpiece unit, receiving a selected voice communication of a first language from the selected microphone and translating the selected voice communication from the first language to a second language, the second language different from the first to create a translated voice communication, and transducing the translated voice communication at a speaker within the earpiece unit. Preferably the microphones are oriented in different directions and are directional microphones. The present invention further optionally provides for the sensing and transmission of pulse oximeter measurements and temperature measurements.

13 Claims, 6 Drawing Sheets

(56) References Cited

U.S. PATENT DOCUMENTS

| | | |
|---|---|---|
| D468,300 S | 1/2003 | Boesen |
| 6,542,721 B2 | 4/2003 | Boesen |
| 6,560,468 B1 | 5/2003 | Boesen |
| 6,664,713 B2 | 12/2003 | Boesen |
| 6,694,180 B1 | 2/2004 | Boesen |
| 6,718,043 B1 | 4/2004 | Boesen |
| 6,738,485 B1 * | 5/2004 | Boesen .......................... 381/312 |
| 6,748,095 B1 * | 6/2004 | Goss ............................. 381/374 |
| 6,754,358 B1 | 6/2004 | Boesen |
| 6,784,873 B1 | 8/2004 | Boesen |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen |
| 2001/0027121 A1 | 10/2001 | Boesen |
| 2002/0010590 A1 * | 1/2002 | Lee ................................ 704/277 |
| 2002/0046035 A1 * | 4/2002 | Kitahara et al. .............. 704/277 |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0065504 A1 * | 4/2003 | Kraemer et al. .................. 704/8 |
| 2004/0160511 A1 | 8/2004 | Boesen |
| 2005/0043056 A1 | 2/2005 | Boesen |
| 2005/0125320 A1 | 6/2005 | Boesen |
| 2005/0148883 A1 | 7/2005 | Boesen |
| 2005/0196009 A1 | 9/2005 | Boesen |

OTHER PUBLICATIONS

Usage Models, The Official Bluetooth Website, printed Jun. 26, 2000.

* cited by examiner

US 8,527,280 B2

VOICE COMMUNICATION DEVICE WITH FOREIGN LANGUAGE TRANSLATION

BACKGROUND OF THE INVENTION

The present invention relates to a voice communication device with foreign language translation. Given the widespread availability of travel the need for foreign language translation has increased. The present invention has applications in numerous areas and instances where foreign language translation is desirable. One particular application of the present invention is in military applications.

U.S. troops have often been required to render assistance in numerous foreign environments. For example, U.S. troops have been used as members of peacekeeping forces in various countries. Further, U.S. troops have been deployed to counter terrorism in the Middle East. In these and other situations, these military personnel are placed at a disadvantage and are potentially subjected to dangers, heightened by the fact that these personnel are unable to speak the native languages used by the people around them. In these types of missions, there is an acute need to be able to understand the locals or natives. The military personnel have a huge and heavy burden of administering justice by neutralizing threats without compromising the safety of innocents in an effort to reduce or eliminate any collateral damage. This places military personnel in a difficult situation.

The identification of potential threats would be aided if the military personnel could understand the language used by the people around them. Knowledge of a foreign language has long been considered an asset in the military. For example, Green Berets are required to speak at least a second language. Nevertheless, given the tenure of today's society where it is not known where conflict may arise and it is not known what language military personnel should be versed in, it is not practical to have sufficient numbers of troops who speak every language that is needed. This problem is further complicated by the fact that there are numerous dialects associated with various languages. Further, even if some troops are skilled in a particular language, it is impractical for every troop to be skilled in that language. Therefore, problems remain.

These same problems are also prevalent in contexts outside of the military. For example, people involved in business, education, and even tourists have reason to speak languages beyond their native tongue. Learning a foreign language can be time-consuming, and many people may not have the time or discipline to do so. Further, many people have the need to communicate in a variety of foreign languages, and it is often impractical for these people to learn every foreign language they might encounter.

Therefore, as a primary object of the present invention to improve upon the state of the art.

It is a further object of the present invention to provide a voice communication device which provides for foreign language translation.

Yet another object of the present invention is to provide a voice communication device which is nonocclusive in nature.

Yet another object of the present invention is to provide a voice communication device that is small and lightweight.

Another object of the present invention is to provide a voice communication device that a soldier can wear in conjunction with a helmet.

Yet another object of the present invention is to provide a voice communication device that is capable of listening in on voice communications that may be outside the range of normal human hearing.

A further object of the present invention is to provide a voice communication device that is capable of listening to voice conversations in multiple directions relative to the operator of the voice communications device.

These and other objects, features, and advantages of the present invention will become apparent from that which is now described.

BRIEF SUMMARY OF THE INVENTION

The present invention includes methods and devices for foreign language translation. According to one embodiment of the present invention, a nonocclusive earpiece that allows the wearer to continue to hear environmental sounds is disclosed. The nonocclusive earpiece includes a plurality of microphones, preferably directional. The directional microphones allow reception of voice communications in microphone positions or orientations relative to the person wearing the earpiece. One of the pluralities of directional microphone may be selected either manually or automatically. Voice sound information received by the corresponding directional microphone can then be amplified and processed. The resulting voice sound information signal is then translated. The translation may occur locally within the earpiece. Alternatively, the translation may occur at a remote location. When translation occurs remotely, the earpiece transmits the selected signal to a translation unit which translates the voice communication and transmits the resulting translation back to the earpiece. The earpiece receives the translation and transduces the translated voice sound information through a speaker disposed within the earpiece.

DETAILED DESCRIPTION OF THE INVENTION

The present invention will now be described as it applies to an exemplary embodiment. It is not intended that the present invention be limited to the described embodiment. It is intended the invention cover all modifications and alternatives which may be included within the spirit and scope of the invention.

Figure 1:
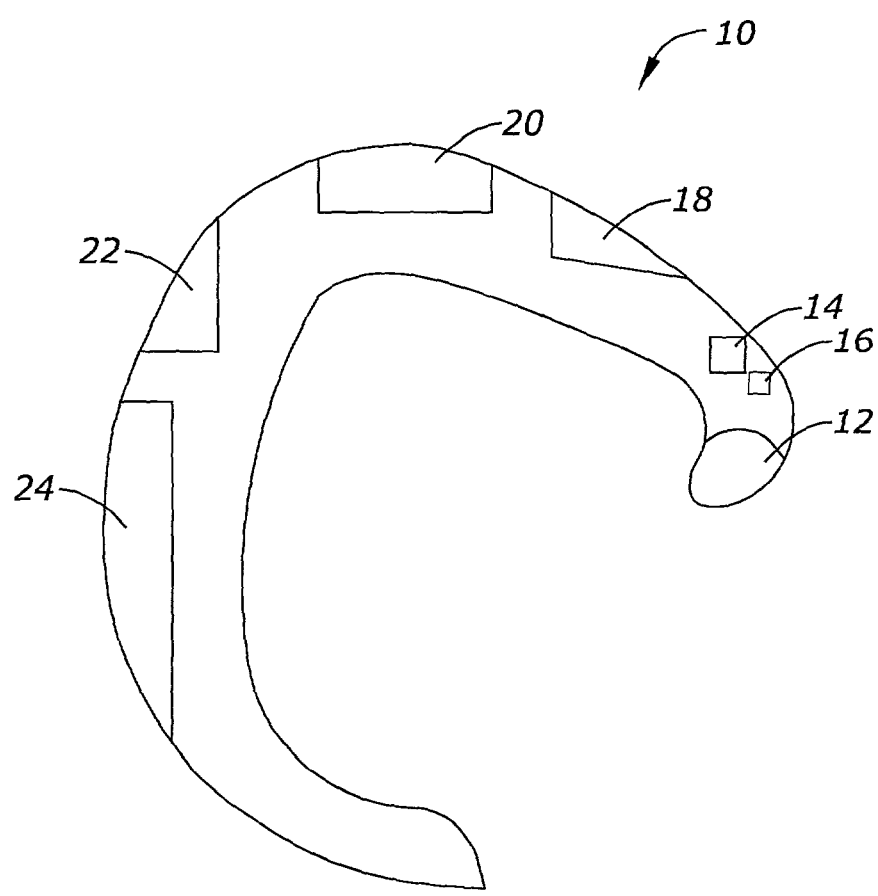
FIG. 1 is a pictorial representation of the nonocclusive earpiece of the present invention.

FIG. 1 shows a front view of one embodiment of an earpiece according to the present invention. The earpiece 10 preferably does not occlude the external auditory canal. The earpiece 10 includes a speaker 12. In addition, the earpiece 10 includes a plurality of microphones. For example, microphones shown include a front microphone 18 directed in a frontward direction, a side microphone 20, directed in an outward direction, and a rear microphone 22, directed in a rearward direction. Each of these microphones is preferably a directional microphone, although omnidirectional microphones may be used. In addition, the earpiece 10 includes an optional pulse oximeter 14 and an optional thermistor 16 or other temperature sensor. The pulse oximeter 14 is placed such that oxygen saturation, and other measurements associated with pulse oximeters are performed. The thermistor 16 provides a body temperature reading. These sensors provide physiological monitoring of the operator. In military applications, such sensors are of great importance, particularly in an era where biological and/or chemical warfare remains a threat. In addition to these optional features, the earpiece unit shown includes an optional expansion slot 24. The expansion slot 24 can be of a variety of structures. The expansion slot 24 allows additions in functionality to be added to the earpiece 10 without replacing the entire earpiece. The expansion slot 24 can receive cards, modules, or other expansion units that provided added features, functionalities, and/or memory such as may be appropriate for a particular use or application.

The earpiece 10 shown in FIG. 1 can be worn under a helmet by military personnel if need be. The relative small size and light weight of the device allow the device to be worn comfortably. Although a behind-the-ear (BTE) earpiece is shown, the present invention further allows for a completely-in-canal (CIC) device also to be worn. Preferably the earpiece does not occlude the external auditory canal of a user. One example of an earpiece that does not occlude the external auditory canal of a user is disclosed in U.S. Pat. No. 6,094,492, herein incorporated by reference in its entirety.

Figure 2:
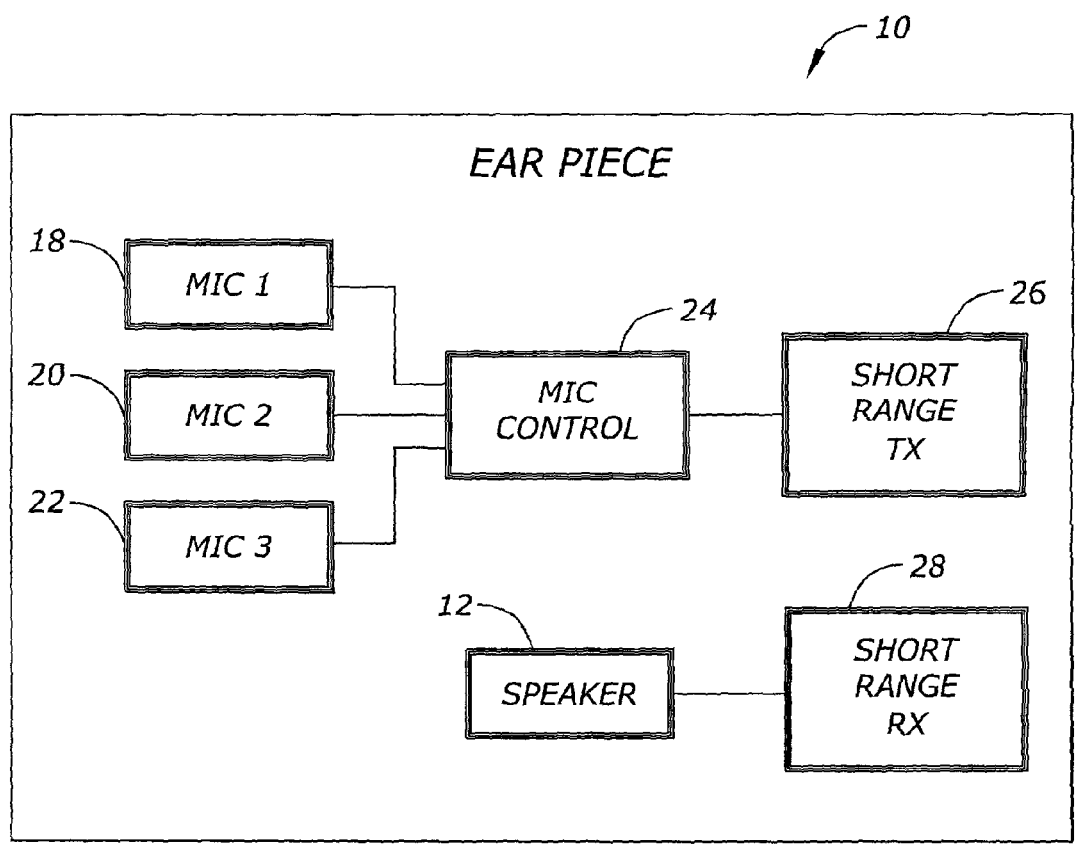
FIG. 2 is a block diagram of the electrical system of one earpiece according to the present invention.

FIG. 2 provides a block diagram of one embodiment of the earpiece of the present invention. As shown in FIG. 2, the earpiece 10 is shown. The earpiece 10 includes a first microphone 18, a second microphone 20, and a third microphone 22. Each of the plurality of microphones is operatively connected to a microphone control unit 24. The microphone control unit 24 is used to manually or automatically select one of the plurality of microphones for transmission over the short-range transceiver 26. The earpiece unit 10 also includes a short range receiver 28 operatively connected to a speaker 12. According to this embodiment of the present invention, one of a plurality of the microphones is selected. The microphone may be selected manually or automatically. The sound information signal associated with that microphone, preferably a voice sound communication, is then transmitted over the short-range transceiver 26. A translated voice sound communication is then received by the short range receiver 28 and then transduced on the speaker 12 such that the wearer of the earpiece 10 hears the translated voice sound information.

Figure 3:
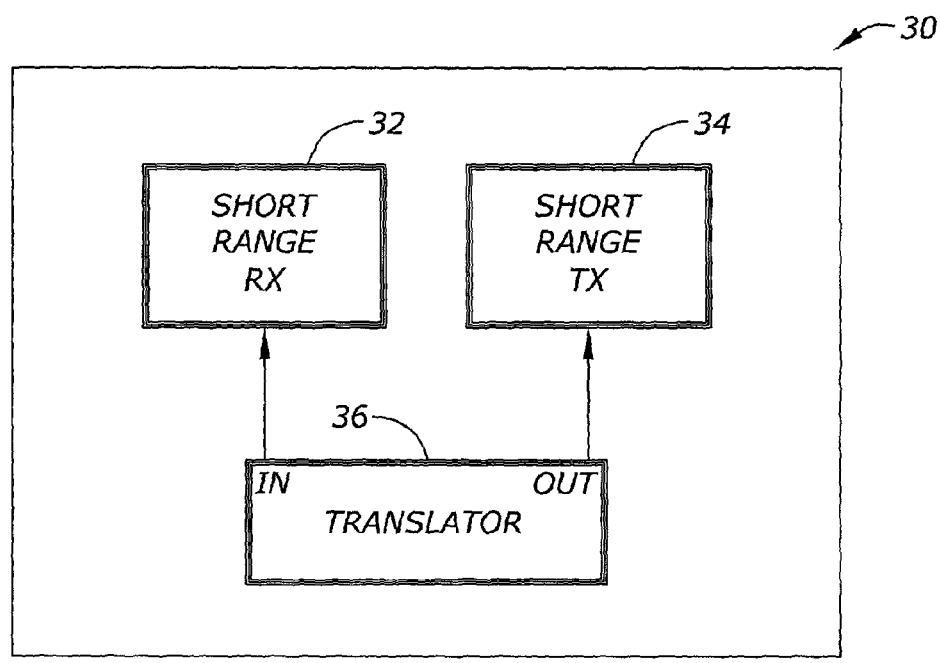
FIG. 3 is a block diagram of one embodiment of the translation station according to the present invention.

FIG. 3 shows a translation unit 30 according to the present invention. As shown in FIG. 3, a short-range receiver 32 is operatively connected to a translator 36. The translator 36 is operatively connected to a short-range transceiver 34. The translator unit 30 receives transmissions of voice sound information of a first language from the earpiece unit 10 at the short range receiver 32, then translates the voice sound information from the first language to a second language and sends the resulting translated voice sound information back to the earpiece unit 10 through the short range transceiver 34. The present invention contemplates numerous variations in the implementation of the translator. In particular, the translator 36 can be a computer adapted for voice translation. Various translator products are available as commercial off-the-shelf products or are available online. Examples include the Franklin language translators, Lernout & Hauspie's Power Translator Pro, and others. The present invention contemplates that the received voice sound information may be processed using voice recognition or other voice to text applications in a first language, and then the resulting text information is then translated to text of a second language. The text of the second language is then converted from text to voice. Preferably such a system is real time or near real time. The present invention is in no way limited to a particular translation method, or language, and allows for any number of such translation methods and languages to be used. The computer used can be a Personal Digital Assistant (PDA), embedded computer, or other computer or electronic device.

Figure 4:
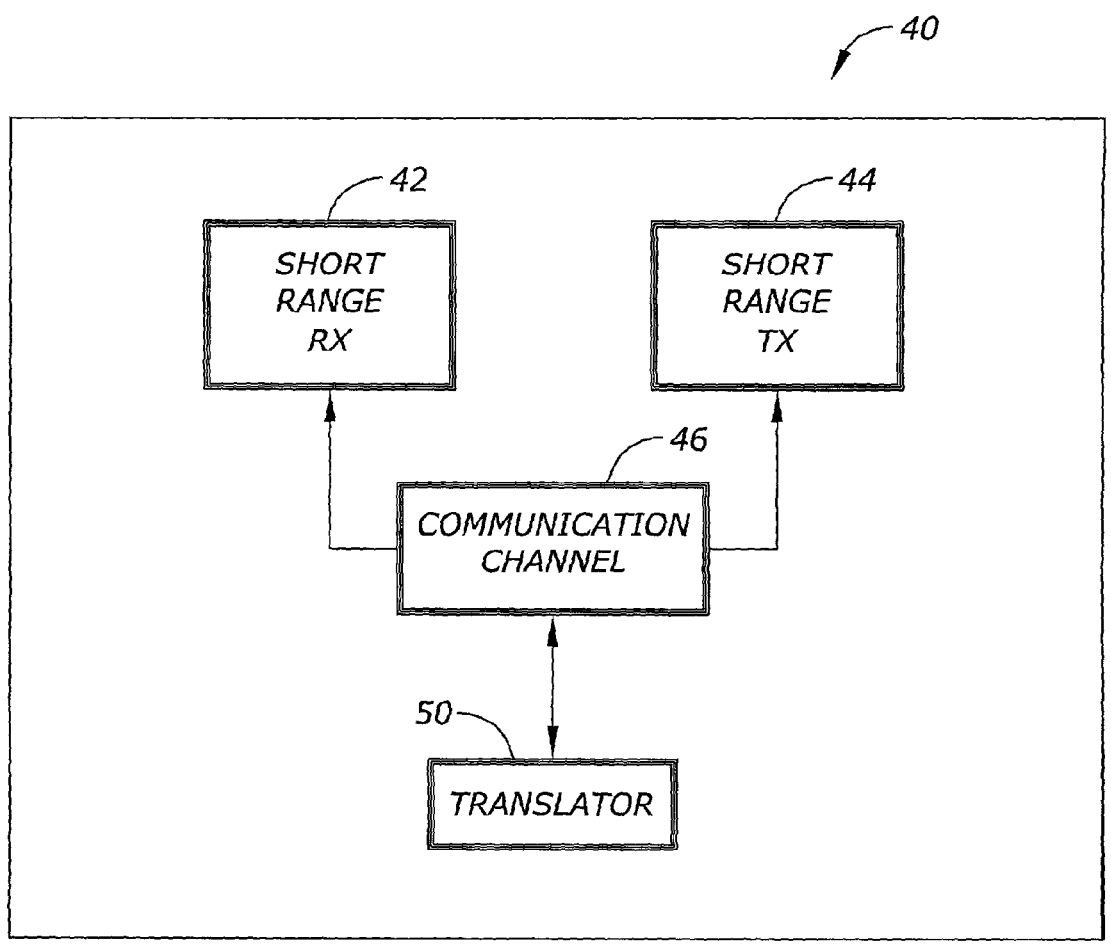
FIG. 4 is a block diagram of another translation system according to the present invention.

FIG. 4 provides a block diagram of another embodiment of the present invention. FIG. 4 provides for a translation system 40 in operative communication with the earpiece unit. In FIG. 4, a short-range receiver 42 receives a voice communication from the earpiece unit. This information is then sent over a communications channel 46 to a translator 50. In this implementation of the present invention, the translator 50 may be at a remote location that is further than a short range from the earpiece unit. The information received from the earpiece is effectively relayed across the communications channel 46. Similarly, information from the translator 50 is effectively relayed across the communications channel 46 back to the short-range transmitter 44 which is in operative communication with the earpiece unit 10. In this embodiment, the computer performing the translation need not be on site and can be well-removed from the earpiece 10 and operator.

Figure 5:
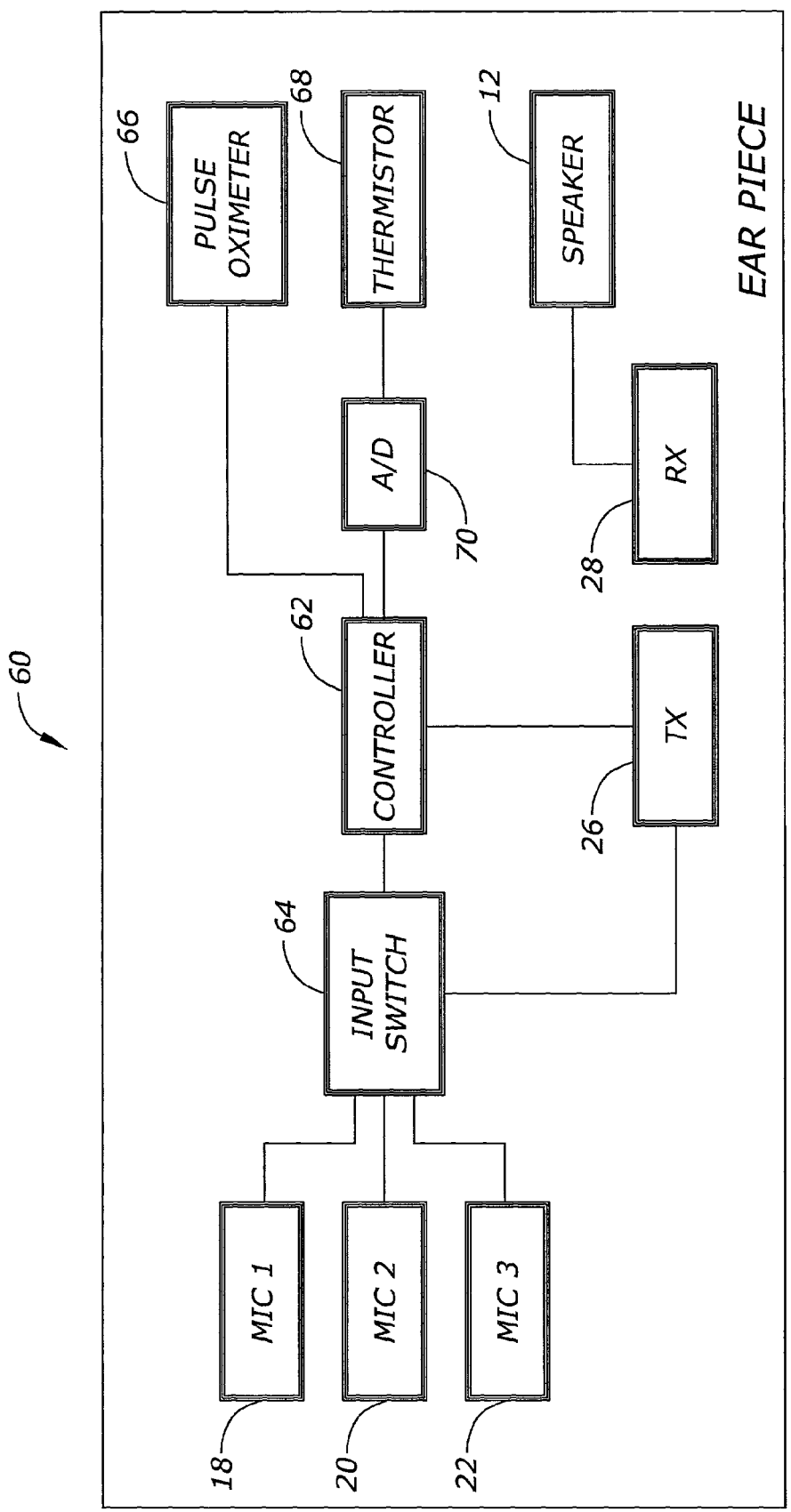
FIG. 5 is a block diagram of an electrical system of another embodiment of the earpiece of the present invention providing physiological monitoring.

FIG. 5 provides a block diagram of another embodiment of the earpiece unit according to the present invention, this embodiment using an input switch 64. In FIG. 5, earpiece unit 60 is shown. The earpiece unit includes a first microphone 18, second microphone 20, and a third microphone 22 electrically connected to an input switch 64. The input switch 64 is one type of microphone control unit that can be used. The input switch 64 routes the output of one of the microphones to the transmitter 26. The input switch 64 allows one of the plurality of microphones to be selected. The input switch 64 is operatively controlled by the controller 62. The controller is an intelligent control. The present invention contemplates any number of types of intelligent controls that can be used according to the present invention. This includes processors, microcontrollers, digital signal processors, integrated circuits, portions of an integrated circuit, control circuits, and other types of intelligent controls. Alternatively, the input switch 64 is manually controlled. The selected input is then relayed to the transmitter 26 which transmits the voice sound communication. The receiver 28 receives the translated voice communication and is capable of outputting the translated voice communication to a speaker 12. In addition, the controller 62 is electrically connected to a pulse oximeter 66 within the earpiece. The pulse oximeter 66 is used to determine oxygen concentration within the blood of the wearer of the earpiece. In addition, a thermistor 68 is electrically connected to the controller 62 such as through an analog to digital converter 70. The analog to digital converter 70 may be built into the controller 62. The present invention provides for information obtained from the pulse oximeter 66 as well as the thermistor 68 to be transmitted with the transmitter 26.

The transmitter 26 provides for the transmission of one or more audio streams such as voice communications from one of the plurality of microphones. In addition, the transmitter preferably allows for the transmission of digital information received from the controller 62. This digital information can include pulse oximeter measurements as well as temperature measurements. In such a transmitter, the transmitter can provide for modulation of the digital data such that both analog and digital information can be received. The present invention also contemplates that the controller 62 can provide the same function if need be by modulating the digital information through pulse width modulation into audio.

Figure 6:
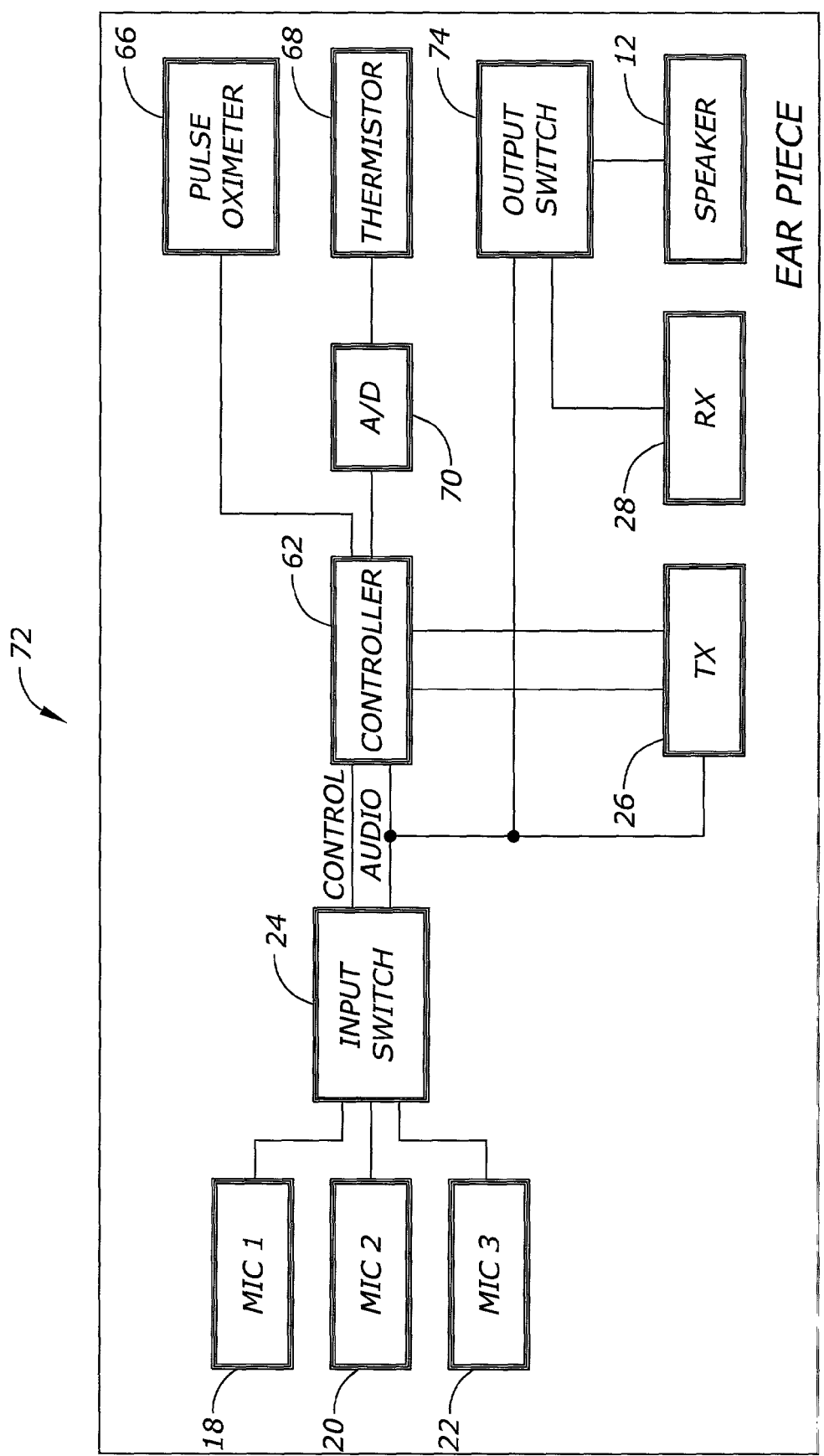
FIG. 6 is another block diagram of an electrical system of one embodiment of the earpiece of the present invention.

FIG. 6 provides a block diagram of another embodiment of the present invention. FIG. 6 illustrates earpiece 72. According to FIG. 6, the present invention provides for the audio received from the selected microphone to be output directly to the speaker 12 as well as to the transmitter 26. The output switch 74 allows this selection to be made. Such a feature is useful when the audio received from the selected microphone is amplified or is otherwise louder or clearer than that which the user would hear without the earpiece. Thus, even if the operator understands the languages being spoken, the present invention still provides advantages.

Figure 7:
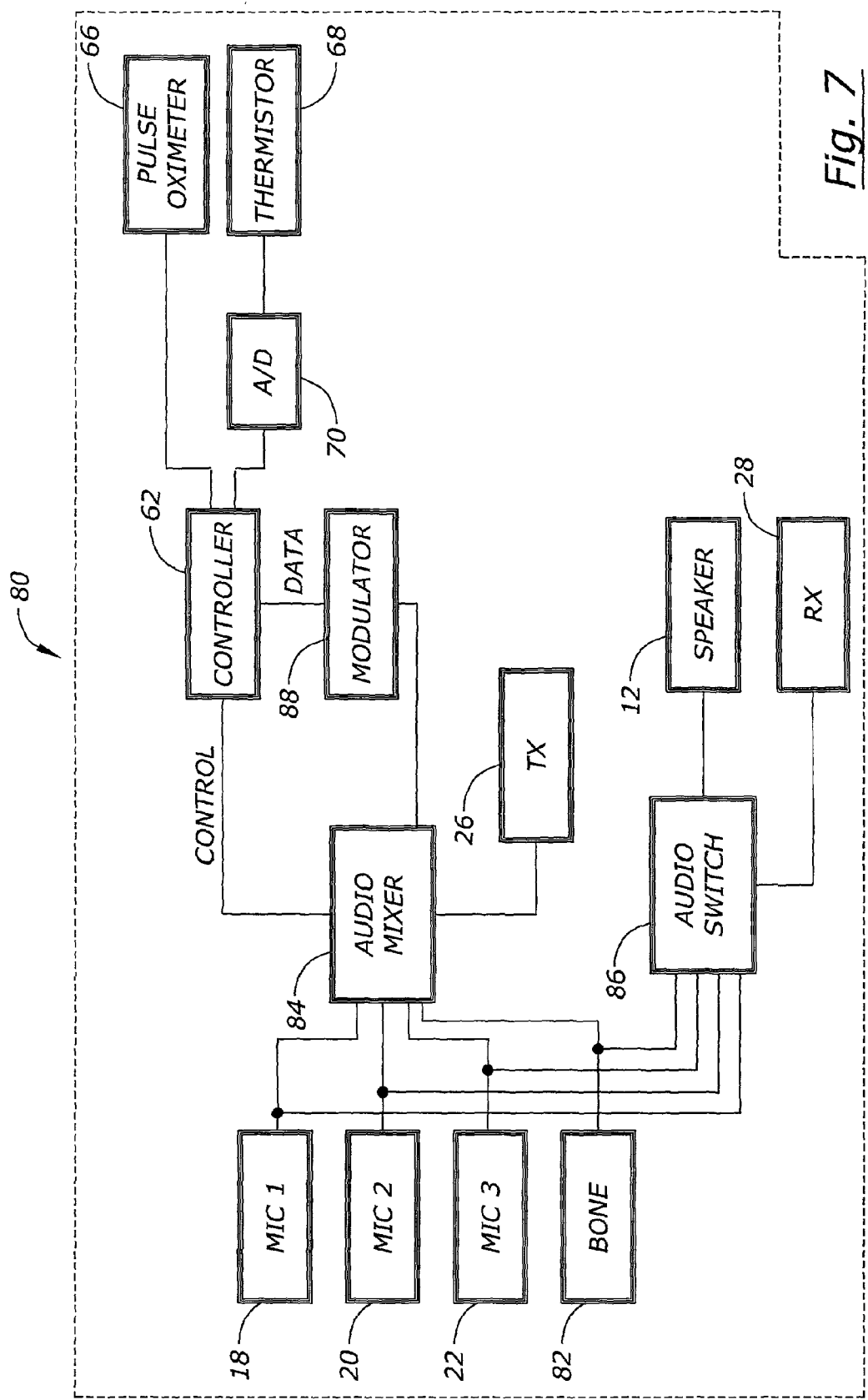
FIG. 7 is another block diagram of one embodiment of the earpiece unit of the present invention.

FIG. 7 is a block diagram of another embodiment of an earpiece 80 of the present invention. In FIG. 7, the earpiece unit includes a bone conduction sensor 82 in addition to a plurality of microphones. Each of the plurality of microphones as well as the bone conduction sensor 82 is electrically connected to an audio mixer 84. The audio mixer 84 allows the signals from each of the microphones as well as the bone conduction sensor 82 to be mixed in various proportions as controlled by the controller 62 which is electrically connected to the audio mixer 84. In addition, the earpiece 80 includes an audio switch 86 electrically connected to each of the microphones and the bone conduction sensor 82. This allows the speaker 12 to transduce any one of the selected signals. Further, a controller 62 is electrically connected to a modulator 88 for combining data into the audio signal which is mixed by audio mixer 84 and transmitted by the transmitter 26. This allows voice communications from the operator, as transduced by the bone conduction sensor 82 or one of the microphones to be communicated. When the bone conduction sensor 82 is used, the operator can speak covertly so that those around the operator can not hear the operator speaking.

Further, the earpiece is preferably nonocclusive in nature. This allows the operator to continue to hear the operator's surroundings even though the operator is also using the earpiece to receive voice communications.

Therefore, a voice communication device with foreign language translation has been disclosed. The present invention contemplates numerous variations in the languages translated, the specific translation product or device used, the number of microphones used, whether a bone conduction sensor, pulse oximeter, and/or temperature sensor are used, whether the translation occurs within the ear piece, within a device that is located within a short range of the ear piece, or by a device located remotely, whether the antenna used be directional or omnidirectional and other variations. The scope of the present invention should be construed broadly and is only to be limited to that which is claimed and all equivalents.

What is claimed is:

1. A method of voice communication comprising:
providing an earpiece having a housing and a plurality of microphones within the earpiece housing, the earpiece adapted for being worn by a user;
selecting at least one microphone within the housing of the earpiece to detect a selected voice communication by a person other than the user;
receiving the selected voice communication of a first language from the at least one selected microphone;
translating the selected voice communication from the first language to a second language by an intelligent control, the second language different from the first to create a translated voice communication, wherein the translating is performed by a processor within the earpiece; and
transducing the translated voice communication at a speaker within the earpiece unit.

2. The method of claim 1 wherein at least one microphone is a directional microphone.

3. The method of claim 1 wherein the step of selecting is automatically selecting.

4. The method of claim 1 further comprising scanning each of the plurality of microphones.

5. The method of claim 1 wherein the plurality of microphones includes a front facing microphone, a rear facing, and a side facing microphone.

6. The method of claim 1 wherein the second language is English.

7. The method of claim 1 wherein the first language is English and the second language is different from the first language.

8. The method of claim 1 wherein the earpiece is nonocclusive.

9. The method of claim 1 wherein the step of selecting is manually selecting.

10. A method of voice communication, comprising:
providing a nonocclusive earpiece housing and having a plurality of inputs for receiving voice communication and a speaker, the nonocclusive earpiece housing adapted for being worn by a user on the user's head;
receiving the voice communication from at least one of the inputs;
translating the voice communication to a different language using an intelligent control to create a translated voice communication;
transducing the translated voice communication at the speaker of the nonocclusive earpiece;
wherein the nonocclusive earpiece further includes a processor;
wherein the processor is adapted to perform translation of the voice communication to the translated voice communication.

11. The method of claim 10 wherein at least one of the inputs is a bone conduction sensor.

12. A method of voice communication comprising:
providing an earpiece having a housing and a plurality of directional microphones within the earpiece housing, the earpiece adapted for being worn by a user;
receiving a selection of at least one of the plurality of directional microphones within the housing of the earpiece, the selection associated with a selected voice communication by a person other than the user;
receiving the selected voice communication of a first language from the selection of the at least one of the plurality of directional microphones;
translating the selected voice communication from the first language to a second language by an intelligent control disposed within the earpiece, the second language different from the first to create a translated voice communication; and
transducing the translated voice communication at a speaker within the earpiece unit.

13. A method of voice communication comprising:
providing a nonocclusive earpiece having a housing and having a plurality of directional microphones within the housing and a speaker within the housing, the earpiece adapted for being worn on a user's head;
directing at least one of the plurality of directional microphones within the earpiece housing in a first direction;
using the at least one of the plurality of directional microphones of the earpiece to detect a selected voice communication;
receiving the selected voice communication of a first language from the at least one of the plurality of directional microphones within the earpiece housing;

translating the selected voice communication at the earpiece from the first language to a second language using a processor disposed within the earpiece, the second language different from the first to create a translated voice communication;
transducing the translated voice communication at the speaker within the earpiece on the user's head.

\* \* \* \* \*